United States Patent [19]

Ensminger et al.

[11] Patent Number: 5,180,365
[45] Date of Patent: Jan. 19, 1993

[54] IMPLANTABLE INFUSION DEVICE

[76] Inventors: William D. Ensminger, 2770 Parkridge Dr.; James A. Knol, 1059 Hasper; James C. Andrews, 3568 River Pines, all of Ann Arbor, Mich. 48103

[21] Appl. No.: 654,661
[22] Filed: Feb. 15, 1991

Related U.S. Application Data

[63] Continuation-in-part of Ser. No. 487,541, Mar. 1, 1990, Pat. No. 5,057,084, and a continuation-in-part of Ser. No. 539,793, Jun. 18, 1990, Pat. No. 5,053,013.

[51] Int. Cl.⁵ ............................................. A61H 11/00
[52] U.S. Cl. .................................... 604/93; 604/167; 604/175
[58] Field of Search ................ 604/167, 175, 93, 244, 604/283, 256, 280

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis et al. . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,387,879 | 6/1983 | Tauschinski . |
| 4,405,320 | 9/1983 | Cracauer et al. . |
| 4,425,119 | 1/1984 | Berglund . |
| 4,430,081 | 2/1984 | Timmermans . |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,543,088 | 9/1985 | Bootman et al. . |
| 4,547,194 | 10/1985 | Moorehead . |
| 4,569,675 | 2/1986 | Prosl et al. . |
| 4,578,061 | 3/1986 | Lemelson . |
| 4,578,063 | 3/1986 | Inmann et al. . |
| 4,581,020 | 4/1986 | Mittleman . |
| 4,623,329 | 11/1986 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |
| 4,781,680 | 11/1988 | Redmond et al. . |
| 4,781,693 | 11/1988 | Martinez et al. . |
| 4,781,695 | 11/1988 | Dalton . |
| 4,790,826 | 12/1988 | Elftman . |
| 4,810,241 | 3/1989 | Rogers . |
| 4,842,591 | 6/1989 | Luther . |
| 4,857,053 | 8/1989 | Dalton . |
| 4,886,501 | 12/1989 | Johnston et al. . |

FOREIGN PATENT DOCUMENTS

| | | |
|---|---|---|
| 0119596 | 3/1984 | European Pat. Off. . |
| 134745 | 8/1984 | European Pat. Off. . |
| 5288787 | 2/1987 | Fed. Rep. of Germany . |
| 3528878 | 2/1987 | United Kingdom . |

OTHER PUBLICATIONS

Rational Drug Therapy, May, 1988, vol. 22, No. 5, William D. Ensminger M.D. and Ira S. Wollner, M.D.

Primary Examiner—John D. Yasko
Attorney, Agent, or Firm—Harness, Dickey & Pierce

[57] ABSTRACT

An infusion port designed for the introduction of a catheter for fluid infusion or removal or other flexible filaments within a patient. The infusion port is buried subcutaneously and accessed using a needle which introduces the filament. The infusion port has means to prevent the introducing needle from being inserted past a certain point within the port whereas the introduced flexible element can be inserted beyond that point and is caused to be forced through an articulating valve. The valve of this disclosure features enhancements in its sealing ability and in some embodiments provides a differing level of frictional engagement with the filament upon insertion versus withdrawal. The infusion port of this invention also has design features which provide a relatively small distance between the surface of the skin and the position of the articulating catheter valve through which the introduced filament passes.

39 Claims, 4 Drawing Sheets

IMPLANTABLE INFUSION DEVICE

CROSS REFERENCE TO RELATED APPLICATIONS

This application is a continuation-in-part of application Ser. No. 487,541 filed on Mar. 1, 1990, now U.S. Pat. No. 5,057,084 and application Ser. No. 539,793 filed on Jun. 18, 1990, now U.S. Pat. No. 5,053,013 both having a title common with this application.

BACKGROUND AND SUMMARY OF THE INVENTION

This invention relates to a device to enable infusing a therapeutic agent to a desired site within a patient, feeding a filament to a desired internal site, or withdrawing a fluid from a patient, and more particularly, to such a device which is implanted such that no portion is transcutaneous. Its access portion is subcutaneous but designed so as to facilitate repeated access by the percutaneous route.

In current human and animal medical practice, there are numerous instances where therapeutic agents must be delivered to a specific organ or tissue within the body. An example is the infusion of chemotherapy into a central vein on a recurring basis over a lengthy treatment period for widespread sites of malignant tumor. Without an infusion device for intravenous drug infusion, multiple vein punctures over a lengthy period result in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an infusion system. Similarly, repeated arterial access is occasionally needed for injection of an X-ray dye or contrast agent into an artery for diagnostic purposes. In other situations, there is a need to remove a body fluid repetitively for analysis from a remote body site. Finally, sensing and physiological measuring devices incorporated into small diameter catheters and small diameter optical fibers are increasingly being utilized for monitoring body processes and could be more easily implemented through a properly designed access device with an adequate internal diameter.

In prior medical practice, percutaneous catheters have been used to provide vascular or organ access for drug therapy or removing body fluids. Although such systems generally performed in a satisfactory manner, numerous problems were presented by such therapy approaches, including the substantial care requirements by patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and are a significant advance over transcutaneous catheters. Presently available infusion ports have a number of common fundamental design features. The ports themselves comprise a housing which forms a reservoir which can be constructed from a variety of plastic or metal materials. A surface of the reservoir is enclosed by a high-density, self-sealing septum, typically made of silicone rubber. Connected to the port housing is an outflow catheter which communicates with a vein or other site within the patient where it is desired to infuse therapeutic agents. Implantation of such devices generally proceeds by making a small subcutaneous pocket in the patient under local anesthesia. The internal outflow catheter is tunnelled to the desired infusion site and is connected to the infusion port. When the physician desires to infuse or remove material through the port, a hypodermic needle is used which pierces the skin over the infusion port and is placed into the port.

Although presently available implantable infusion ports generally operate in a satisfactory manner, they have a number of shortcomings. Since these devices rely on a compressed rubber septum for sealing, there are limitations in the diameter of needles which can be used to penetrate the septum, since large diameter needles can seriously damage the septum. Moreover, the needles used must be of a special design which minimizes septum damage. These diameter limitations severely restrict the flow rate of fluids passing through the port.

For prolonged infusion using a conventional port, the infusion needle is taped to the patient's skin to hold it in position. Conventional ports do not allow the needle to penetrate deeply into the port; consequently a small displacement of the needle can cause it to be pulled from the port, allowing extravasation. In cases where locally toxic materials are being infused, extravasation of such materials can cause local tissue damage which can lead to a requirement for corrective surgery such as skin grafting or removal of tissue.

Presently available implantable drug infusion devices must also have a significant size to provide an acceptable target surface area for the physician who must locate the port and penetrate the septum properly with a needle. The port housing becomes bulky as the septum size increases since structure is required to maintain the septum in compression to provide self-sealing after the needle is removed. Moreover, presently available infusion ports are difficult to clear if thrombosis occurs within them or in the implanted outflow catheter, since it is difficult if not impossible to feed a cleaning wire through the penetrating hypodermic needle in a manner which will clear the infusion device and the internal outflow catheter. Present infusion ports have a space which contains a retained fluid volume beneath the self-sealing septum which increases the volume of drug which must be administered to enable a desired quantity to reach the infusion site. This retained volume also poses problems when a physician desires to deliver different drugs to the same infusion site which are incompatible when mixed. In addition, when it is desired to withdraw blood through the port, the retained volume of the prior art infusion ports is an area where blood clotting can occur, thus interfering with future access to the site. And finally, for present infusion ports, there is a risk that the physician attempting to pierce the port septum will not properly enter it, leading to the possibility of extravasation which can cause significant undesirable consequences as mentioned previously.

The present invention relates to an implantable infusion port which provides numerous enhancements over prior art devices. In accordance with this invention, an infusion port is provided which incorporates a funnel-shaped entrance orifice which narrows down to a reduced diameter passageway. The passageway communicates with an internal cavity which retains an articulating catheter valve such as a multi-element leaflet valve assembly. The port passageway is also connected to an implanted catheter. The infusion ports of the present invention are adapted to be used in conjunction with a sharp hypodermic access needle of conventional design which introduces a filament into the port such as a catheter, guide wire, optical fiber etc.

In one series of embodiments in the group of inventions described in the related applications, the port was primarily intended to be accessed by a blunt introducer fed through a slit wound on the patient. These embodiments are primarily described in the parent application Ser. No. 487,541.

In another series of embodiments of this invention, first described and claimed in a prior related application Ser. No. 539,793, the port entrance orifice guides a needle into a guide passageway and through a catheter valve. For those designs, the reduced diameter guide passageway of the port housing accurately aligns the needle to strike the catheter valve at a desired area so that a needle can be used to penetrate the catheter valve repeatedly without impairing the function of the valve.

The convenient access to the port and internal outflow catheter provided by this invention enables these elements to be cleared with a wire, avoiding the problem of permanent impaction of prior art devices. In addition, the ability to feed a guide wire into the infusion port and internal catheter of this invention enables the internal catheter to be repositioned using a bent or "steerable" guide wire.

The infusion ports having an articulating catheter valve of this invention possess the advantage that they have a very small reservoir or "dead space", meaning that virtually all of the infused fluid is throughput to the desired infusion site. This invention, therefore, facilitates infusion of incompatible materials in a serial fashion since very little of the previously infused fluid remains in the device when a subsequent infusion is carried out. The ports of this invention also permit an introduced catheter or other filament to be deeply inserted into the internal outflow catheter which reduces the possibility of small displacement of the introduced filament preventing it from being withdrawn from the port during infusion.

In addition to permitting access using generally conventional techniques as mentioned above, this application describes additional features of infusion ports beyond those described in the two prior related applications. One area of potential improvement for some purposes is the provision of a port designed for implantation in a patient's arm which has an access passageway for an inserted needle. The body of this port is angled upwardly slightly to facilitate access. Such an angled infusion port can also feature modifications to the entrance orifice to again further enhance the ability to access the implanted port. This application further describes a valving concept for an implanted port which provides a high degree of resistance to body fluid leakage through the port and further provides a relatively low level of friction upon insertion of an external catheter with a relatively higher degree of friction upon withdrawal of the catheter. This difference in resistance aids both in insertion of the catheter and in maintaining the catheter in an inserted condition within the implanted port.

This application also describes port design features which are best embodied in a port in which the entrance funnel is in a plane generally parallel to the mounting base of the port (i.e. the accessing needle penetrates perpendicular to the mounting base). One improvement for such ports is the provision of a physical feature such as a projecting lug, flange or other protuberance which enables the clinician to determine the orientation of the implanted port through tactile examination. By knowing the port orientation the needle and introduced filament can often be more readily inserted into the port. This series of ports also known as a "chest wall" port (named for a preferred usage) also features a funnel-shaped entrance orifice having a progressively changing included angle. The orifice starts at its outer periphery with a relatively shallow included angle which increases toward its center. This progressive change in cone angle provides two significant benefits. First, it results in a port which has a relatively shallow funnel which reduces the distance between the skin surface and the catheter valve which seals around the introduced catheter and also serves to better orient and hold the introducing needle. The port according to this continuation-in-part application also features a means for stopping the introduced needle before reaching the catheter valve but permitting the introduced catheter to pass through the catheter valve.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
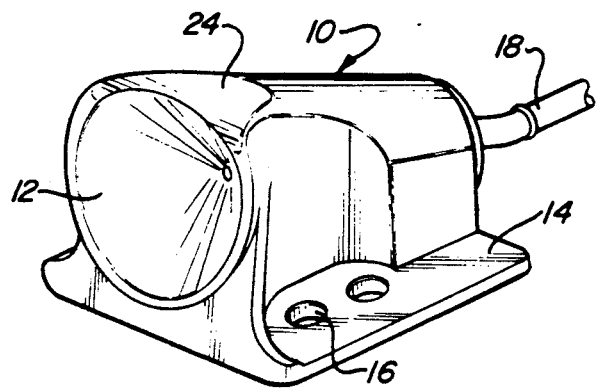
FIG. 1 is a pictorial view of an angled infusion port.
Figure 2:
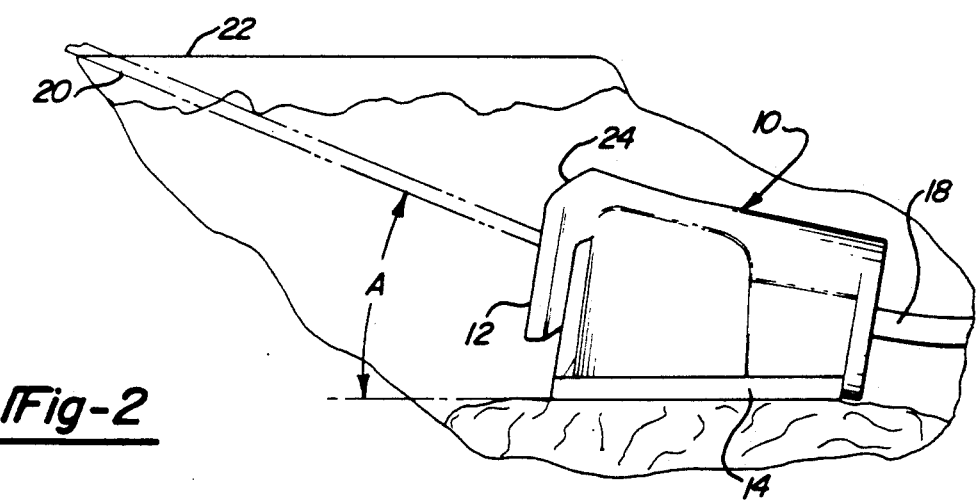
FIG. 2 is a side view of the port shown in FIG. 1 shown implanted within a patient and being accessed by a penetrating needle.

An infusion port in accordance with the first embodiment of this application is shown in FIGS. 1 and 2 and is generally designated there by reference number 10. Infusion port 10 is generally similar to that shown in the application Ser. No. 539,793 which is related to the present application. Port 10 is designed to be accessed using a sharp needle which passes into the port through funnel shaped entrance orifice 12. Port 10 also includes a mounting pad 14 defining a generally planer mounting surface and having apertures 16 for sutures or staples to enable the device to be secured to appropriate support tissue within the patient. Internal catheter 18 is shown attached to port 10 and is tunneled to a desired site within the patient.

The embodiment shown in FIGS. 1 and 2 of this application is presented to disclose two specific improvements to a device described in the aforementioned related patent application, namely a modified entrance orifice 12 and inclination of the device with respect to mounting pad 14. As best shown in FIG. 2, infusion port 10 is oriented such that the accessing needle 20 shown in phantom lines enters the device at an angle, designated as angle A from a plane parallel to mounting pad 14. The inclined orientation of port 10 facilitates insertion of needle 20 through the patients skin 22, as shown in FIG. 2.

The further improvement shown in FIGS. 1 and 2 for infusion port 10 involves a removal of the upper surface of the housing in the area defining entrance orifice 12 shown as a scalloped region 24. Removing material in that area has the effect of slightly enlarging the target area of entrance orifice 12, and also to provide a smoother surface which is covered by the patients skin, thus making the device somewhat less conspicuous to the patient and possibly less irritating.

Although the features of infusion port 10 discussed in conjunction with FIGS. 1 and 2 are employed in a port of the type shown in FIG. 1 of parent application Ser. No. 539,793, these improvements could also be incorporated into ports having various constructions and internal features including other ports which are described in this application and disclosed in the related applications.

Figure 3:
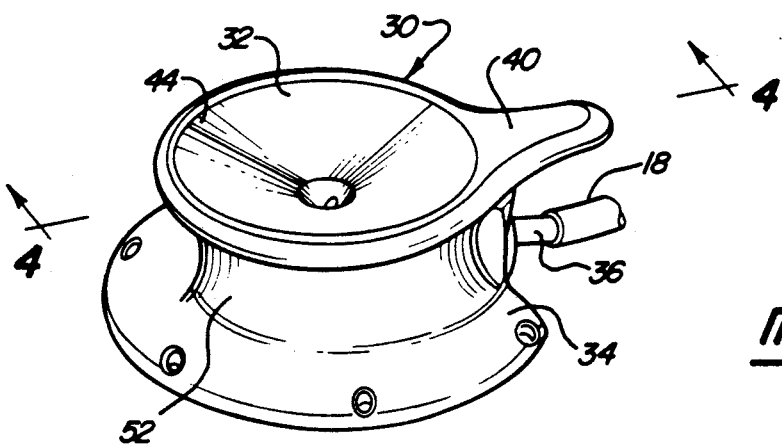
FIG. 3 is a pictorial view of another embodiment of an infusion port according to this invention.

FIG. 3 illustrates infusion port 30 in accordance with a second embodiment of this invention. Infusion port 30 is primarily intended to be implanted in the chest wall region of a patient and generally comprises a funnel shaped entrance orifice 32, mounting platform 34, outlet tube 36, and a valving system which will be described in the following description.

Mounting platform 34 features apertures 38 for enabling port 30 to be secured to underlying tissue within a patient using sutures, staples, etc.

As best shown in FIG. 3, infusion port housing 52 also features a radially projecting protuberance in the form of a lug or ledge 40 projecting away from entrance orifice 32, and overlying outlet tube 36. By providing such an irregular feature on the device housing 52, the orientation of the port, and in particular, outlet tube 36 and internal catheter 18 can be readily ascertained through palpation of the device by the clinician. As will be better described in the following paragraphs, for some embodiments it is necessary to cause the introduced filament to undergo a rather sharp turn upon entrance into the device, and, therefore, knowing the orientation of the port can aid in feeding in the introduced filament. Lug 40 also provides the additional benefit of shielding implanted catheter 18 from needle sticks by the accessing hypodermic needle 20, if improperly aimed.

Figure 4:
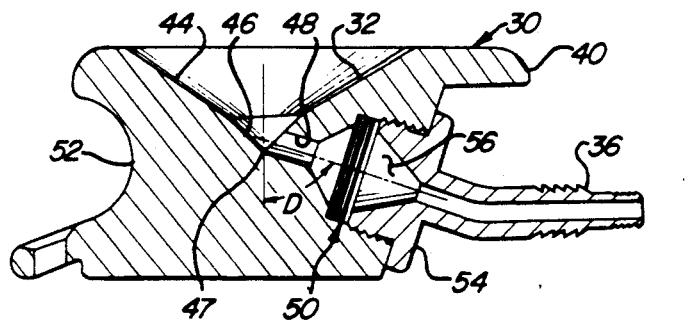
FIG. 4 is a cross-sectional view taken along line 4—4 from FIG. 3.
Figure 6:
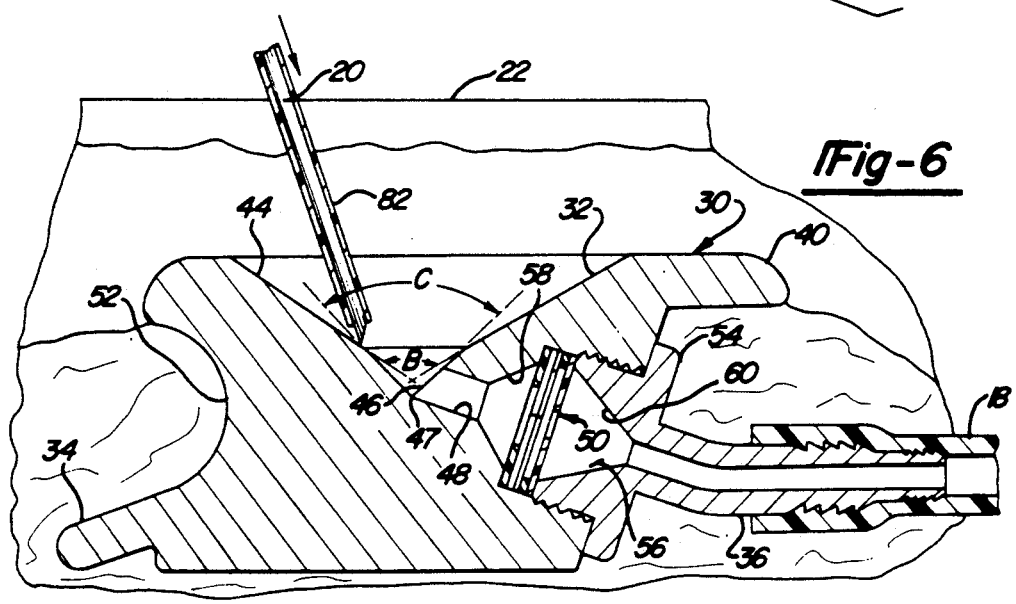
FIG. 6 is an enlarged cross-sectional view similar to FIG. 4 but showing an accessing needle being introduced into the port.

Now with reference to FIGS. 4 and 6, the configuration of entrance orifice 32 can be described in more detail. As is apparent from the figures, entrance orifice 32 is in the form of a pair of joined conical surfaces having differing cone angles. The first conical surface 44 which forms the outer perimeter of the orifice defines a relatively shallow cone having a relatively large included cone angle identified as angle B in FIG. 6. Conical surface 44 joins with a smaller diameter conical surface 46 having an included angle identified as angle C in the Figure which is smaller than angle B. The shallower conical surface 44 is provided as a means of guiding inserted needle 20 toward the apex or focus area 47 of orifice 12. The relatively large angle B of conical surface 44 is provided so that the distance through infusion port 30 between its top planer surface and the internal valve system is kept as small as reasonably possible while providing a large target area for needle 20. This total distance is significant in that presently employed catheters which are fed over needles have a relatively short length, i.e. approximately two inches. It is desirable to allow such existing needles and catheters to be used with port 30, and at the same time, insure that the introduced catheter is securely inserted into the infusion port and engaged with the internal valve. Conical surface 46 is provided with a smaller included angle as a means of securely engaging introduced needle 30 and restraining it from radial motion once it is inserted and becomes rested in focus area 47.

While the benefits of the configuration of entrance orifice 12 are achieved in accordance with the illustrated embodiment using two joined conical segments, it is fully within the scope of this invention to provide an entrance orifice defined by various other surfaces having a progressively decreasing cone angle as measured as shown in FIG. 6 when moving from the outer perimeter of entrance orifice 32 to the focus area 47. For example, a paraboloid surface could also be provided for orifice 32. In addition, entrance orifice 32 could be defined by a surface which is a asymmetrical in the sense of not being a surface of revolution about an axis through the orifice. Many surfaces can be imagined providing the benefits of the invention through providing a progressively smaller cone angle or target surface as the focus area is approached.

As is shown in FIG. 6 the relatively large angle of conical surface 44 serves to provide a low height between the upper surface of infusion port 30 and articulating catheter valve 50. As mentioned previously, this is advantageous since standard introduced catheters have a relatively short length and it is desirable to make sure they are fully engaged with the articulating valve to preclude inadvertent withdrawal.

The focus area 47 of entrance orifice 32 joins with entrance passageway 48 which leads to an articulating catheter valve assembly 50. For reasons which will be better described later in this specification, passageway 48 is intentionally oriented with respect to the central generating axis of entrance orifice 32 at a relatively great off-axis angle, shown as angle D in FIG. 4 of about 60 degrees. This off-axis orientation provides a curved passageway which is intended to prevent an introduced rigid needle 20 from undergoing the turn and directly engaging articulating catheter valve assembly 50. This feature accordingly distinguishes infusion port 30 from the embodiments described previously in this application and in the related applications which are either designed to be used with a blunt accessing instrument, or enable the inserted needle to pass directly through the articulating valve.

Housing 52 is preferably made from a hard metal material which will not be gouged or engaged by the accessing needle 20. For example, Titanium or another hard metal could be used to form the entrance housing 52, or could be used merely to form the surface of entrance orifice 32.

As best shown in FIGS. 4 and 6, infusion port housing 52 and outlet plug 54 define catheter valve cavity 56. As shown in the Figures, cavity 56 is bounded by a pair of conical surfaces including conical surface 58 which joins with passageway 48, and conical surface 60 formed by outlet plug 54. As shown in the figures, the included angle defined by conical surface 58 is greater than that of conical surface 60. The conical surfaces 58 and 60 are provided to enable flexing of the elements comprising articulating catheter valve 50.

Figure 5:
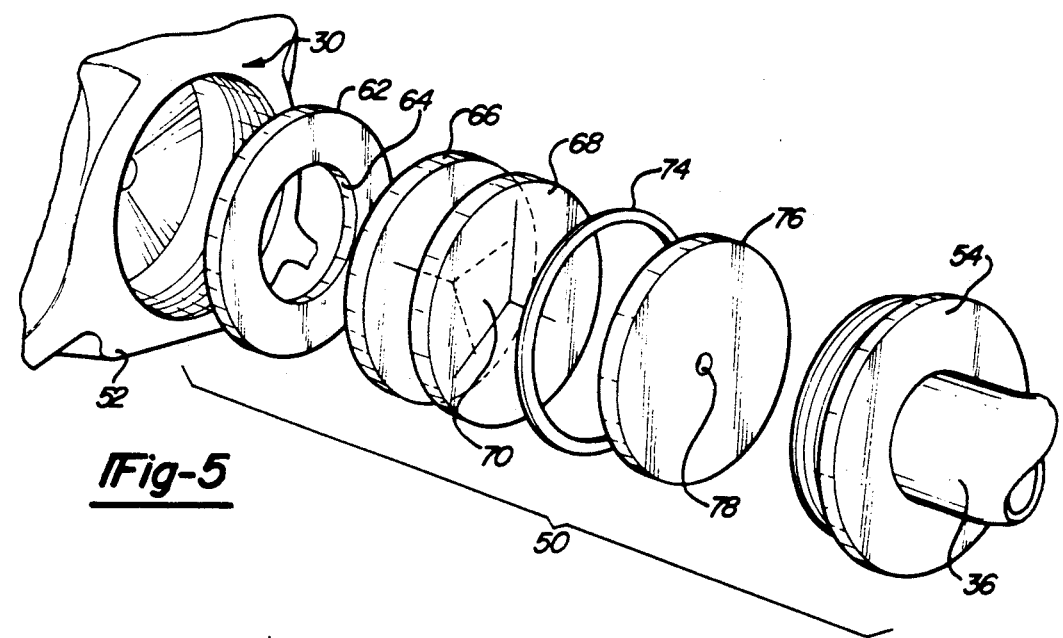
FIG. 5 is an exploded pictorial view of the catheter valve of the port shown in FIGS. 3 and 4.

FIG. 5 provides an exploded view of articulating catheter valve assembly 50. The valve is comprised of a number of individual valve elements stacked together. The first valve element encountered when passing through valve 50 from entrance orifice 32, is a ring or donut valve 62, which is comprised of a ring of elastomeric material such as silicone rubber with a central circular aperture 64. Infusion port 30 can be used with introduced catheters of various diameters. Ring valve 62 is not provided to seal directly against the outer periphery of all sizes of introduced catheters, but rather provides a reinforcing function for the remaining catheter valve elements and also serves to orient and center the introduced catheter, as will be described in more detail below. The next two valve elements are leaflet valve discs 66 and 68. Valve discs 66 and 68 each define three or more leaves 70 which form an apex at the geometric center of each valve disc. As shown in FIG. 5, the leaves of each valve disc 66 and 68 are intentionally disaligned or indexed to an offset position so that the leaves are not directly overlapping. This indexing is provided to enhance the sealing capabilities of catheter valve 50. The next elements encountered in valve 50 are spacer ring 74 and finally another ring or donut valve 76 with central aperture 78. Aperture 78 has a diameter which is slightly smaller than any of the catheters which infusion port 30 is designed to be used with, thus providing a firm perimeter seal for the introduced catheters. The elements comprising catheter valve 50 are stacked together, inserted into valve cavity 56 and retained there through the threaded engagement between housing 52 and outlet plug 54.

Since hollow post 36 of outlet plug 54 is not oriented parallel to the plane defining mounting pad 14, the hollow post is bent slightly as shown in FIG. 4 as a means of orienting implanted catheter 18 along the plane defining port mounting platform 34.

FIGS. 6 through 9 are provided to show infusion port 30 in use, and in particular, show the process of introducing an external catheter into the device. FIG. 6 shows infusion port 30 implanted within a patient below the surface of skin 22. In FIG. 6, a hypodermic needle 20 is shown penetrating skin 22. Needle 20 is placed through catheter 82 of conventional design such as that known as an angiocath. Needle 20 and catheter 82 are inserted through the skin and into entrance orifice 32. Conical surface 44 initially guides the needle into conical surface 46, and finally into nesting engagement in focus area 47. As stated previously, orifice 12 is made from a material which will not be gouged by needle 20, but rather will guide it into focus area 47.

Figure 7:
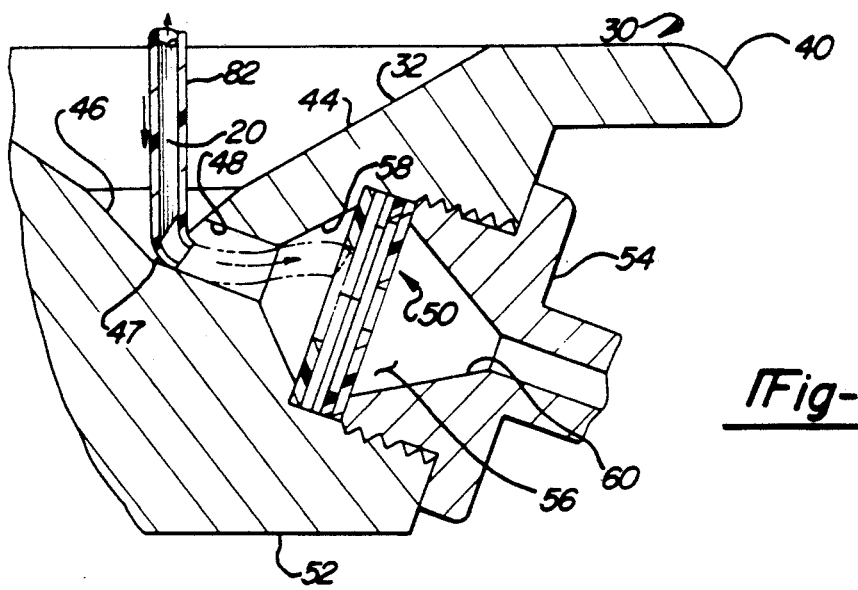
FIG. 7 is a partial cross-sectional view showing the accessing needle and catheter being more fully inserted into the port.

FIG. 7 shows accessing needle 20 being fully inserted into focus area 47 and into passageway 48. Due to the inclination of passageway 48 from the entrance orifice, needle 20 cannot readily pass beyond the point shown in FIG. 7. Once this position is reached, the clinician has positive feedback that the elements are oriented properly since it is apparent that the needle cannot be readily inserted any further into infusion port 10.

Figure 9:
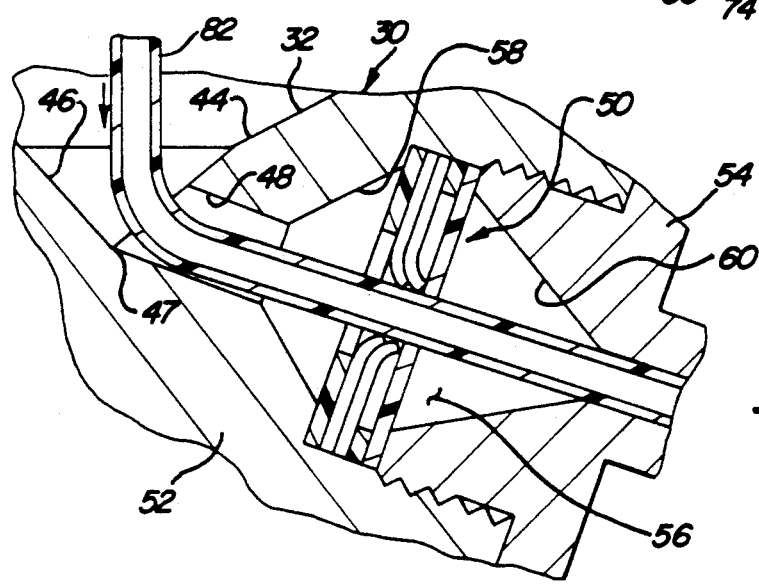
FIG. 9 is a partial pictorial view showing an introduced catheter completely passing through the articulating valve and in a proper docking position with the port for material infusion.

Once the point of FIG. 7 is reached, the clinician can slide catheter 82 along needle 20 while holding the needle in position, thus forcing the tip of catheter 82 further into infusion port 30. FIG. 7 illustrates in phantom lines that external catheter 82 undergoes a bend as it is fed into engagement with valve 50. Catheter 82 does not necessarily become oriented precisely along the longitudinal axis of passageway 48 and, therefore, does not always initially engage articulating catheter valve assembly 50 at its center. Ring valve element 62 serves to aid in centering introduced catheter 82 to properly orient itself with respect to the remaining valve elements. As introduced catheter 82 is forced further into engagement with the catheter valve 50, it passes through leaflet valve discs 66 and 68. As discussed in the prior related applications, the leaves 70 can be readily opened by inserting the external catheter and their triangular shape serves to aid in centering the catheter. Finally, the introduced catheter passes through second ring valve element 76 having a relatively small aperture 78. Due to the centering functions provided by ring element 62 and the leaflet element 66 and 68, the introduced catheter becomes accurately aligned with and forced through aperture 78. Aperture 78 is sized to provide a perimeter seal around the introduced catheter 82. A fully inserted catheter is shown in FIG. 9.

Figure 8:
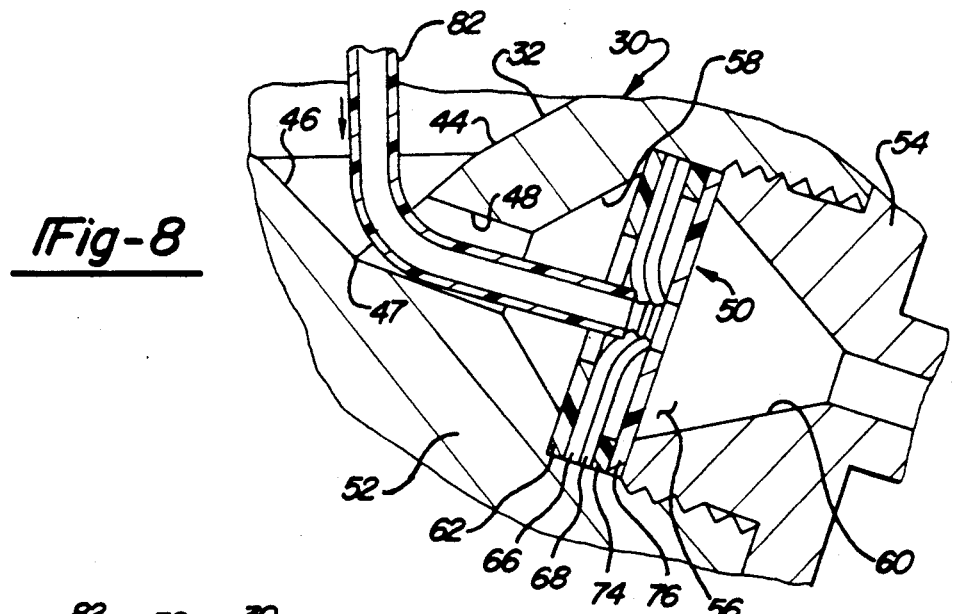
FIG. 8 is a partial cross-sectional view showing the introduced catheter penetrating the valve assembly of the port.

The design of articulating catheter valve 50 according to this invention provides a number of significant features. By providing spacing ring 74, deflection of leaflet valve leaves 70 in the direction of the insertion of catheter 82 is freely permitted. When the introduced catheter passes through the leaflet valves, leaves 70 are permitted to deflect as shown in FIGS. 8 and 9 without significant restriction caused by the presence of ring valve element 76. However, upon withdrawal of introduced catheter 82, reverse deflection of valve leaves 70 causes them to be reinforced by the close proximity of valve element 62, thus providing a relatively greater amount of friction during withdrawal versus insertion of catheter 82. This difference in insertion versus withdrawal friction is a desirable feature since it allows the catheter to be freely inserted into the port, yet firmly engages the inserted catheter to prevent inadvertent withdrawal of it during infusion.

The differing cone angles provided by catheter valve cavity conical surfaces 58 and 60 also provide several functions. The relatively large angle of conical surface 58 is provided to place the passageway 48 in close proximity to catheter valve 50. This enhances the "targeting" function to ensure that catheter 82 strikes the catheter valve 50 at or near its center where it can be easily deflected and is guided into a proper engagement with ring valve element 76. This large cone angle also serves to limit the degree of deflection of ring valve element 62, thus increasing withdrawal friction. The relatively small cone angle of conical surface 60 is provided to guide the introduced catheter smoothly into hollow post 80 and provides clearance to permit relatively unrestricted deflection of leaflet valves 66 and 68 and ring valve element 76.

Figure 10:
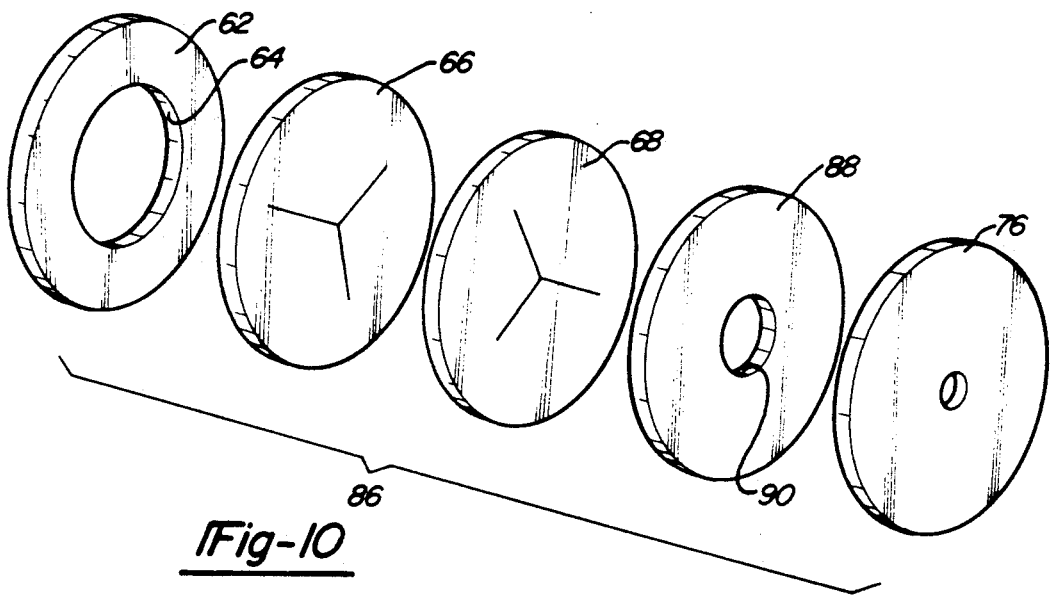
FIG. 10 is an exploded pictorial view of an articulating catheter valve according to a second embodiment of this invention.

FIG. 10 shows in alternate embodiment of an articulating catheter valve assembly designated by reference number 86. Catheter valve assembly 86 has a number of elements identical to catheter assembly 50 described previously, and the common elements are designated by common reference numbers. Catheter valve assembly 86 differs from the previous embodiment in that spacer ring 74 is replaced with another donut or ring valve element 88, having an internal circular aperture 90. The function of ring valve element 88 is to reinforce leaves 70 of valve disc 68 as a means of enhancing the sealing capabilities of catheter valve assembly 86. The diameter of aperture 90 is chosen to be larger than any introduced catheter 82 with which valve assembly 86 would be used.

Figure 11:
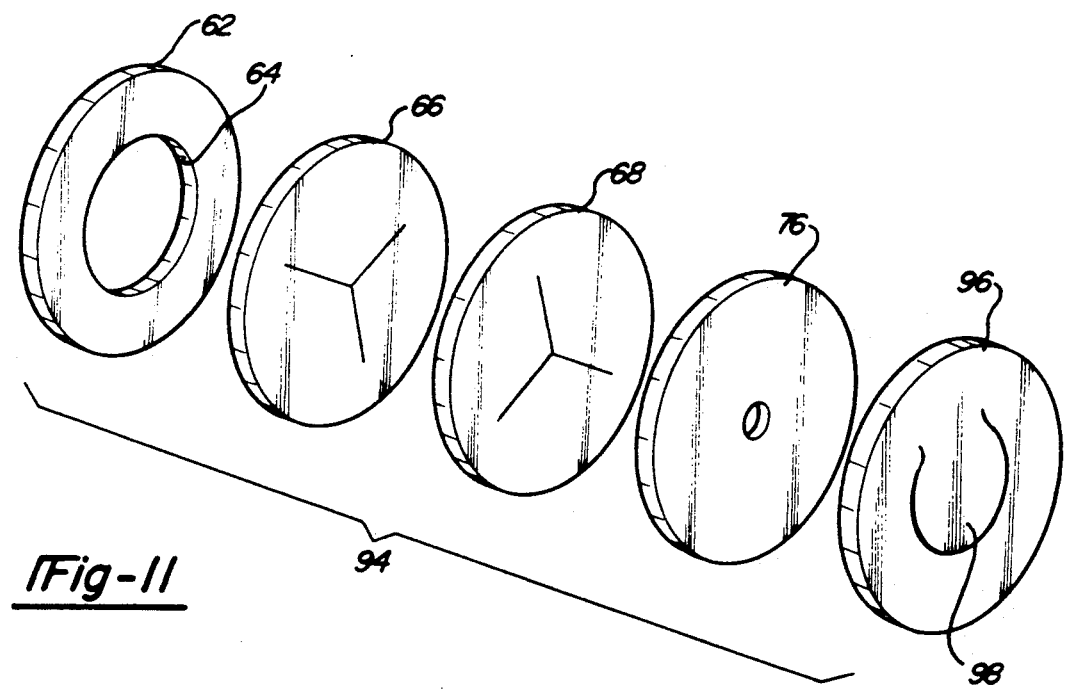
FIG. 11 is an exploded pictorial view of an articulating catheter valve according to a third embodiment.

FIG. 11 shows yet another embodiment of a catheter valve assembly according to this invention designated by reference number 94. This embodiment also features a number of elements common to that of catheter valve assembly 50 which are identified by like reference numbers. Catheter valve 94, however, features a flapper type valve element 96 having a central flap or leaf 98. Flapper valve 96 is provided to act as a check valve providing enhanced resistance to reverse fluid leakage since flap 98 is actuated by fluid pressure into sealing engagement with valve disc 76. Flap 98 is readily deflected upon the insertion of catheter 82 or another flexible introduced filament.

While the above description constitutes the preferred embodiments of the present invention, it will be appreciated that the invention is susceptible of modification, variation and change without departing from the proper scope and fair meaning of the accompanying claims.

We claim:

1. An implantable infusion port for allowing the introduction of a flexible filament such as a catheter wire or optical fiber into a patient and being accessed using a needle which penetrates the patient's skin with said filament being introduced into the port by said needle, comprising:

housing means defining an enlarged generally funnel shaped entrance orifice, with the surface of said entrance orifice formed of a hard material to guide said needle contacting said orifice to a focus area, mounting means for fastening said port subcutaneously, an entrance passageway formed by said housing means extending from said focus area to a valve chamber and to an exit passageway communicating with a site within the patient, valve means within said valve chamber for permitting said filament to pass through said valve means while restricting the flow of fluids across said valve means when said filament is removed, and stop means within said entrance passageway between said focus area and said valve chamber for restricting the passage of said needle while permitting said flexible filament to pass through said entrance passageway and engage said valve means.

2. An implantable infusion port according to claim 1 wherein said stop means comprises a bend in said entrance passageway.

3. An implantable infusion port according to claim 1 wherein said entrance orifice defines a surface having a first included cone angle adjacent the outside perimeter of said entrance orifice and defining a second included cone angle adjacent said focus area which is smaller than said first included cone angle.

4. An implantable infusion port according to claim 3 wherein said first and second included cone angles are formed by joined conical surfaces.

5. An implantable infusion port according to claim 1 wherein said housing means entrance orifice has a central axis generally perpendicular to the patient's skin and further defines a projection which can be detected by external palpation after said port is implanted which indicates the orientation of said port.

6. An implantable infusion port according to claim 1 wherein said valve means comprises an articulating catheter valve.

7. An implantable infusion port according to claim 6 wherein said articulating catheter valve includes at least two leaflet valve elements each defining multiple leaves stacked together with at least one of said leaflet valve elements having three or more leaves with said leaves of each of said leaflet valve elements oriented such that said leaves are disaligned to enhance sealing of said valve.

8. An implantable infusion port according to claim 7 further comprising at least one ring valve element placed on one said of said leaflet valve elements.

9. An implantable infusion port according to claim 8 wherein said ring valve element is positioned on the side of said leaflet valve elements confronting said exit passageway.

10. An implantable infusion port according to claim 8 wherein said ring valve element is positioned on the side of said leaflet valve elements confronting said entrance orifice focus area.

11. An implantable infusion port according to claim 8 further comprising a spacer ring placed between said leaflet valve elements and said ring valve element.

12. An implantable infusion port according to claim 1 wherein said valve means imposes less friction upon said filament being inserted through said valve means than imposed upon said filament upon withdrawal of said filament.

13. An implantable infusion port for allowing the introduction of a flexible filament such as a catheter wire or optical fiber into a patient and being accessed using a needle which penetrates the patient's skin with said filament being introduced into the port by said needle, comprising:

a housing having a generally funnel shaped entrance orifice having a focus area and defining a surface having a first included cone angle around the outer perimeter of said entrance orifice and defining a second included cone angle adjacent said focus area smaller than said first included cone angle, said surface of said entrance orifice being formed of a hard material enabling said needle upon contacting said entrance orifice to be guided toward said focus area, and means for mounting said port subcutaneously.

14. An implantable infusion port according to claim 13 wherein said first and second included cone angles are defined by joined conical surfaces.

15. An implantable infusion port according to claim 13 further comprising an articulating catheter valve within said housing for permitting said filament to pass into an entrance passageway and through said valve and to an exit passageway while restricting the flow of fluids across said valve when said filament is removed from said port.

16. An implantable infusion port according to claim 15 wherein said housing further defines stop means within said entrance passageway for restricting said needle from engaging said articulating catheter valve.

17. An implantable infusion port according to claim 16 wherein said stop means comprises a bend in said entrance passageway.

18. An implantable infusion port according to claim 13 wherein said housing entrance orifice has a central axis generally perpendicular to the patient's skin and further defines a projection which can be detected by external palpation after said port is implanted which indicates the orientation of said port.

19. An implantable infusion port according to claim 15 wherein said articulating catheter valve includes at least two leaflet valve elements each defining multiple leaves stacked together with at least one of said leaflet valve elements having three or more leaves with said leaves of each of said leaflet valve elements oriented such that they are disaligned to enhance sealing of said valve.

20. An implantable infusion port according to claim 19 further comprising at least one ring valve element placed on one side of said leaflet valve elements.

21. An implantable infusion port according to claim 19 further comprising a ring valve element positioned on the side of said leaflet valve elements confronting said exit passageway.

22. An implantable infusion port according to claim 20 wherein said ring valve element is positioned on the side of said leaflet valve elements confronting said entrance orifice focus area.

23. An implantable infusion port according to claim 20 further comprising a spacer ring placed between said leaflet valve elements and said ring valve element.

24. An implantable infusion port according to claim 15 wherein said valve imposes less friction upon said filament being inserted through said valve than imposed upon said filament upon withdrawal of said filament.

25. An implantable infusion port for allowing the introduction of a flexible filament such as a catheter wire or optical fiber into a patient and being accessed using a needle which penetrates the patient's skin with said filament being introduced into the port by said needle, comprising:
   a housing defining a generally funnel shaped entrance orifice leading to a focus area,
   an entrance passageway formed by said housing extending from said focus area to a valve chamber and to an exit passageway communicating with a preselected site within the patient,
   a valve installed within said valve chamber for permitting the passage of said filament while resisting the flow of fluids across said valve when said filament is removed from said port, and said valve having at least two leaflet valve elements each having three or more leaves, with at least one ring valve element stacked against one of said leaflet valve elements.

26. An implantable infusion port according to claim 25 wherein said ring valve element is positioned between said leaflet valve elements and said entrance orifice to aid in guiding said filament through said valve.

27. An implantable infusion port according to claim 25 wherein said ring valve element is positioned between said leaflet valve elements and said exit passageway against said leaflet valve elements for supporting said leaflet valve element leaves.

28. An implantable infusion port according to claim 25 wherein said ring valve element is positioned between said leaflet valve elements and said exit passageway and is spaced from said leaflet valve elements to permit said leaves of said leaflet valve elements to freely deflect upon insertion of said filament.

29. An implantable infusion port according to claim 25 comprising first and second ring valve elements positioned between said leaflet valve elements and said exit passageway wherein said first ring valve element supports said leaves of said leaflet valve elements and said second ring valve element defines a perimeter seal around said filament.

30. An implantable infusion port according to claim 25 wherein said valve further comprising a flapper valve element.

31. An implantable infusion port according to claim 25 further comprising stop means within said entrance passageway between said focus area and said valve chamber for restricting the passage of said needle while permitting said introduced filament to pass through said entrance passageway and engage said valve.

32. An implantable infusion port according to claim 31 wherein said stop means comprises a bend in said entrance passageway.

33. An implantable infusion port according to claim 25 wherein said entrance orifice defines a surface having a first included cone angle around the outside perimeter of said entrance orifice and defining a second included cone angle around said focus area which is smaller than said first included cone angle.

34. An implantable infusion port according to claim 33 wherein said first and second included cone angles are defined by joined conical surfaces.

35. An implantable infusion port according to claim 25 wherein said housing means entrance orifice has a central axis generally perpendicular to the patient's skin and further defines a projection which can be detected by external palpation after said port is implanted which indicates the orientation of said port.

36. An implantable infusion port according to claim 25 wherein said valve imposes less friction upon said filament being inserted through said valve than imposed upon said filament upon withdrawal of said filament.

37. An implantable infusion port for allowing the introduction of a flexible filament such as a catheter, wire or optical fiber into a patient and being accessed using a needle which penetrates the patient's skin with said filament being introduced into the port by said needle, comprising:
   a housing having an entrance orifice for receiving said filament, and
   valve means for permitting said filament to pass through said housing but restricting the flow of fluids across said valve means when said filament is removed from said port, said valve means further for imposing greater friction on said filament upon removal of said filament from said port as compared with insertion of said filament.

38. An implantable infusion port according to claim 37 wherein said valve means includes at least one leaflet valve element having leaves which deflect when said filament is placed through said valve means, and means for allowing said leaves to deflect more readily in the direction of insertion of said filament as compared to removal of said filament.

39. An implantable infusion port for allowing the introduction of a flexible filament such as a catheter wire or optical fiber into a patient and being accessed using a needle which penetrates the patient's skin with said filament being introduced into the port by said needle, comprising:

housing means defining an enlarged generally funnel shaped entrance orifice defining a central axis which intersects with a narrowed down focus area of said orifice, valve means within said housing for permitting said filament to pass through said valve means while restricting the flow of fluids across said valve means when said filament is removed, and mounting means for mounting said port subcutaneously, said mounting means defining a mounting plane, and wherein said entrance orifice central axis forms an acute angle with respect to said mounting plane for facilitating access to said port by said needle.

* * * * *

UNITED STATES PATENT AND TRADEMARK OFFICE
CERTIFICATE OF CORRECTION

PATENT NO. : 5,180,365
DATED : January 19, 1993
INVENTOR(S) : William D. Ensminger, et al It is certified that error appears in the above-identified patent and that said Letters Patent is hereby corrected as shown below:

Column 9, Line 34 Claim 1 after "catheter" insert --,--

Column 10, Line 39 Claim 13 after "catheter" insert --,--

Column 11, Line 37, Claim 25 after "catheter" insert --,--

Column 12, Line 66, Claim 39 after "Catheter" insert --,--

Signed and Sealed this

Twenty-third Day of November, 1993

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO.  :  5,180,365

DATED       :  January 19, 1993

INVENTOR(S) :  William D. Ensminger, James A. Knol, James C. Andrews

It is certified that error appears in the above-identified patent and that said Letters Patent is hereby corrected as shown below:

Column 9, line 44, Claim 1, "an entrance passageway" should be the beginning of a new paragraph.

Signed and Sealed this

Twenty-ninth Day of March, 1994

Attest:

BRUCE LEHMAN

Attesting Officer

Commissioner of Patents and Trademarks